US00PP21687P2

(12) United States Plant Patent
Crocker

(10) Patent No.: US PP21,687 P2
(45) Date of Patent: Feb. 1, 2011

(54) ***CAMELLIA* PLANT NAMED 'MONDEL'**

(50) Latin Name: *Camellia sasanqua*
Varietal Denomination: Mondel

(75) Inventor: Brad Crocker, Ladera Ranch, CA (US)

(73) Assignee: Monrovia Nursery Company, Inc., Azusa, CA (US)

( * ) Notice: Subject to any disclaimer, the term of this patent is extended or adjusted under 35 U.S.C. 154(b) by 0 days.

(21) Appl. No.: 12/653,200

(22) Filed: Dec. 9, 2009

(51) Int. Cl.
*A01H 5/00* (2006.01)

(52) U.S. Cl. ..... Plt./243
(58) Field of Classification Search ..... Plt./243
See application file for complete search history.

*Primary Examiner*—Annette H Para
(74) *Attorney, Agent, or Firm*—C. A. Whealy

(57) ABSTRACT

A new and distinct cultivar of *Camellia* plant named 'MonDel', characterized by its compact and upright plant habit; freely branching habit; freely flowering habit; relatively long flowering period; single pink-colored flowers; and good garden performance.

1 Drawing Sheet

Botanical designation: *Camellia sasanqua.*
Cultivar denomination: 'MONDEL'.

BACKGROUND OF THE INVENTION

The present Invention relates to a new and distinct cultivar of *Camellia* plant, botanically known as *Camellia sasanqua,* and hereinafter referred to by the name 'MonDel'.

The new *Camellia* plant originated as a naturally-occurring whole plant mutation of *Camellia sasanqua* 'Yuletide', not patented. The new *Camellia* plant was discovered and selected by the Inventor as a single flowering plant from within a population of plants of 'Yuletide' in a controlled outdoor nursery environment in Azusa, Calif. in November, 1999.

Asexual reproduction of the new *Camellia* plant by terminal cuttings taken in a controlled greenhouse environment in Azusa, Calif. since 2006, has shown that the unique features of this new *Camellia* plant are stable and reproduced true to type in successive generations.

SUMMARY OF THE INVENTION

Plants of the new *Camellia* have not been observed under all possible environmental conditions. The phenotype may vary somewhat with variations in environment such as temperature and light intensity without, however, any variance in genotype. The following traits have been repeatedly observed and are determined to be the unique characteristics of 'MonDel'. These characteristics in combination distinguish 'MonDel' as a new and distinct cultivar of *Camellia:*

1. Compact and upright plant habit.
2. Freely branching habit.
3. Freely flowering habit.
4. Relatively long flowering period.
5. Single pink-colored flowers.
6. Good garden performance.

Plants of the new *Camellia* differ from plants of the female parent, 'Yuletide', in the following characteristics:

1. Plants of the new *Camellia* have pink-colored flowers whereas plants of 'Yuletide' have red-colored flowers.

2. Plants of the new *Camellia* flower for a longer period of time than plants of 'Yuletide'.

Plants of the new *Camellia* can be compared to the plants of *Camellia sasanqua* 'Setsugekka', not patented. In side-by-side comparisons conducted in Azusa, Calif., plants of the new *Camellia* differed from plants of the 'Setsugekka' in the following characteristics:

1. Plants of the new *Camellia* were more compact than plants of 'Setsugekka'.
2. Plants of the new *Camellia* were more suitable for containers than plants of 'Setsugekka'.
3. Plants of the new *Camellia* and 'Setsugekka' differed in flower form and color as plants of 'Setsugekka' had semi-double white-colored flowers.
4. Plants of the new *Camellia* flower for a longer period of time than plants of 'Setsugekka'.

BRIEF DESCRIPTION OF THE PHOTOGRAPHS

The accompanying colored photographs illustrate the overall appearance of the new *Camellia* plant. These photographs show the colors as true as it is reasonably possible to obtain in colored reproductions of this type. Colors in the photographs may differ slightly from the color values cited in the detailed botanical description, which accurately describe the colors of the new *Camellia* plant.

The photograph at the top of the first sheet comprises a side perspective view of a typical flowering plant of 'MonDel' grown in a container.

The photograph at the bottom of the sheet is a close-up view of a typical flower of 'MonDel'.

DETAILED BOTANICAL DESCRIPTION

The aforementioned photographs and following observations and measurements describe plants grown in Visalia, Calif. in one-gallon containers in a polypropylene-covered shadehouse during the autumn under commercial production conditions. During the production of the plants, day temperatures ranged from 24° C. to 26° C. and night temperatures ranged from 8° C. to 12° C. Plants were pinched one time and were 42 months old when the photographs and description were taken. In the following description, color references are made to The Royal Horticultural Society Colour Chart, 2007, except where general terms of ordinary dictionary significance are used.

Botanical classification: *Camellia sasanqua* 'MonDel'.

Parentage: Naturally-occurring whole plant mutation of *Camellia sasanqua* 'Yuletide', not patented.

Propagation:

*Type.*—By vegetative cuttings.

*Time to root cuttings, summer.*—About four to six months at soil temperatures of 23° C. to 26° C. and air temperatures of 32° C. to 37° C.

*Time to root cuttings, winter.*—About four to six months at soil temperatures of 18° C. and air temperatures of 21° C. to 23° C.

*Root description.*—Fleshy, medium in thickness; creamy yellow in color.

*Rooting habit.*—Moderate branching; moderately dense.

Plant description:

*Plant form and growth habit.*—Perennial evergreen shrub; compact and upright plant habit; vigorous growth habit.

*Branching habit.*—Freely branching habit; about six to seven primary lateral branches develop per plant each with numerous secondary laterals; pinching enhances lateral branch development.

*Plant height.*—About 50 cm.

*Plant diameter, area of spread.*—About 24 cm.

*Lateral branch description.*—Length: About 32 cm. Diameter: About 6 mm. Internode length: About 1.5 cm to 2 cm. Strength: Strong. Texture, young stems: Slightly pubescent. Texture, older stems: Woody. Color, young stems: Close to N199C. Color, older stems: Close to 199B.

*Foliage description.*—Arrangement: Alternate, single. Length: About 4.6 cm. Width: About 2.4 cm. Shape: Elliptical. Apex: Acute. Base: Attenuate. Margin: Serrulate. Venation pattern: Pinnate, arcuate. Texture, upper surface: Smooth, glabrous. Texture, lower surface: Mostly smooth and glabrous with short hairs long the mid-vein. Color: Developing leaves, upper surface: Close to N137A. Developing leaves, lower surface: Close to 137A. Fully expanded leaves, upper surface: Darker than 139A; venation, close to 147A. Fully expanded leaves, lower surface: Close to N137A; venation, close to 146A.

*Petiole.*—Length: About 5 mm. Diameter: About 2 mm. Texture, upper and lower surfaces: Pubescent. Color, upper and lower surfaces: Close to 137B.

Flower description:

*Flower arrangement and appearance.*—Single rotate flowers, flowers terminal and axillary; freely flowering habit with usually about four to five flowers and flower buds per apex; flowers face mostly upright; flowers initially cupped and flattening with development.

*Natural flowering season.*—Long flowering period, plants of the new *Camellia* flower continuously from October to January in California.

*Postproduction longevity.*—Plants maintain good flower substance for about seven to ten days on the plant; flowers persistent.

*Fragrance.*—Moderately fragrant; vanilla-like.

*Flower diameter.*—About 7.5 cm.

*Flower depth.*—About 2.2 cm.

*Flower bud.*—Length: About 2.8 cm. Diameter: About 1.6 cm. Shape: Ovoid. Color: Close to 67C.

*Petals.*—Arrangement: Single flower form; about ten petals arranged in two to three whorls. Length: About 3.8 cm. Width: About 2.3 cm. Shape: Obovate. Apex: Rounded. Base: Attenuate. Margin: Entire. Texture, upper and lower surfaces: Smooth, glabrous; velvety. Color: When opening, upper surface: Close to 73C. When opening, lower surface: Close to 55B to 55C. Fully opened, upper surface: Close to 73C; towards the base, close to 55B; color becoming closer to 73D with development. Fully opened, lower surface: Close to 73C; towards the base, close to 73B.

*Sepals.*—Arrangement: About five to seven fused in two whorls; cup-shaped calyx. Length: About 1.2 cm. Width: About 1.1 cm. Shape: Ovate to broadly elliptical. Apex: Broadly acute. Base: Truncate. Margin: Entire. Texture, upper surface: Smooth, glabrous. Texture, lower surface: Pubescent. Color, upper surface: Close to 145A to 145B. Color, lower surface: Close to 144A to 144B.

*Peduncles.*—Length: About 4 mm. Diameter: About 3 mm. Aspect: About 30° from vertical. Strength: Strong. Texture: Smooth, glabrous. Color: Close to 145B.

*Reproductive organs.*—Androecium: Quantity per flower: About 78. Filament length: About 1.7 cm. Filament color: Close to 4C. Anther shape: Oval. Anther length: About 2 mm. Anther color: Close to 162D. Pollen amount: Scarce. Pollen color: Close to 15A. Gynoecium: Quantity of pistils per flower: One. Pistil length: About 1 cm. Style length: About 5 mm. Style color: Close to 145C. Stigma shape: Four-parted. Stigma color: Close to 145C. Ovary color: Close to 145C to 145D.

*Fruits/seeds.*—Fruit and seed production have not been observed on plants of the new *Camellia*.

Garden performance: Plants of the new *Camellia* have been observed have good garden performance and to be tolerant to rain and wind and to tolerate temperatures from about 9° C. to about 43° C.

Disease/pest tolerance: Plants of the new *Camellia* have been observed to be have good tolerance to Petal Blight, *Anthracnose,* Camellia Rust Mite, Red Mites and Aphids. Plants of the new *Camellia* have not been observed to be tolerant or resistant to other pathogens and pests common to *Camellias.*

It is claimed:

1. A new and distinct cultivar of *Camellia* plant named 'MonDel' as illustrated and described.

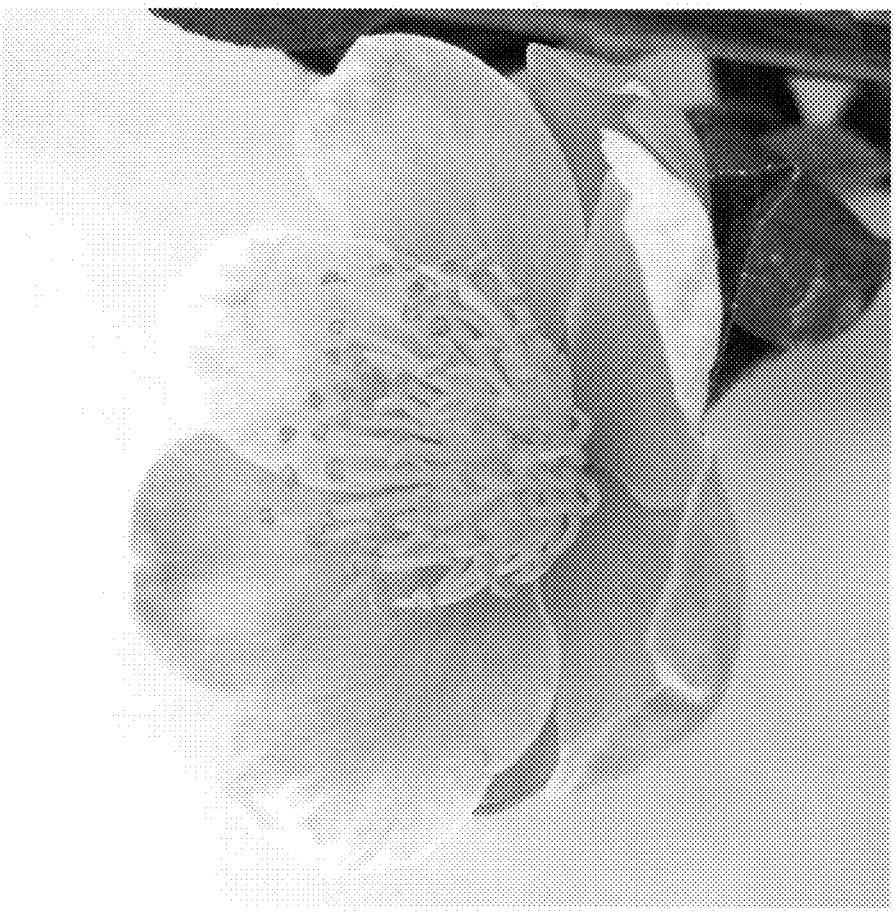
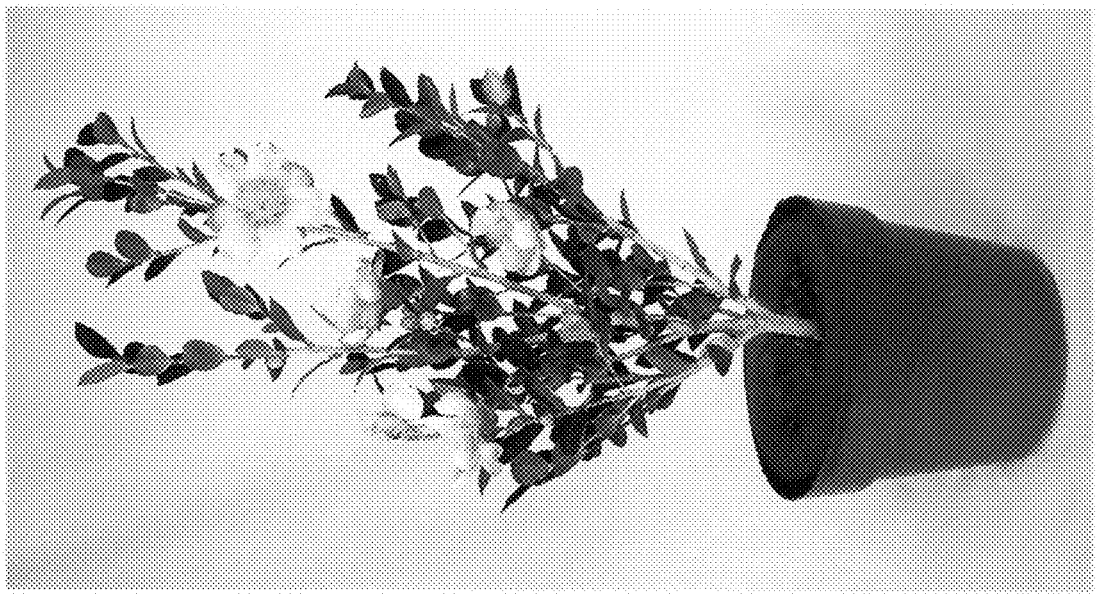

* * * * *